(12) United States Patent
Capone et al.

(10) Patent No.: US 11,642,300 B2
(45) Date of Patent: May 9, 2023

(54) METHOD OF SELECTING SKIN TREATMENT REGIMENS, INGREDIENTS AND COMPOSITIONS

(71) Applicant: Johnson & Johnson Consumer Inc., Skillman, NJ (US)

(72) Inventors: Kimberly Capone, Lambertville, NJ (US); Janeta Nikolovski, Princeton, NJ (US); Lorena Telofski, Skillman, NJ (US); Georgios Stamatas, Issy-les-Moulineaux (FR)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 16/871,670

(22) Filed: May 11, 2020

(65) Prior Publication Data

US 2020/0360259 A1 Nov. 19, 2020

Related U.S. Application Data

(60) Provisional application No. 62/848,042, filed on May 15, 2019.

(51) Int. Cl.

| | |
|---|---|
| *A61K 8/64* | (2006.01) |
| *A61K 8/34* | (2006.01) |
| *A61K 8/36* | (2006.01) |
| *A61K 8/41* | (2006.01) |
| *A61K 8/42* | (2006.01) |
| *A61K 8/44* | (2006.01) |
| *A61K 8/49* | (2006.01) |
| *A61K 8/55* | (2006.01) |
| *A61Q 5/02* | (2006.01) |
| *A61Q 19/00* | (2006.01) |
| *A61Q 19/10* | (2006.01) |

(52) U.S. Cl.
CPC ............ *A61K 8/64* (2013.01); *A61K 8/345* (2013.01); *A61K 8/361* (2013.01); *A61K 8/41* (2013.01); *A61K 8/42* (2013.01); *A61K 8/44* (2013.01); *A61K 8/442* (2013.01); *A61K 8/445* (2013.01); *A61K 8/447* (2013.01); *A61K 8/4913* (2013.01); *A61K 8/55* (2013.01); *A61Q 5/02* (2013.01); *A61Q 19/007* (2013.01); *A61Q 19/10* (2013.01)

(58) Field of Classification Search
CPC .......... A61K 8/64; A61K 8/345; A61K 8/361; A61K 8/41; A61K 8/42; A61K 8/44; A61K 8/442; A61K 8/445; A61K 8/447; A61K 8/4913; A61K 8/55; A61Q 5/02; A61Q 19/007; A61Q 19/10; G01N 33/92; G01N 2333/4742; G01N 33/5088; G01N 2800/20
See application file for complete search history.

(56) References Cited

U.S. PATENT DOCUMENTS 9,808,408 B2 * 11/2017 Stella ................. A61K 8/96
2018/0185255 A1 * 7/2018 Wei ..................... A61Q 19/10

* cited by examiner

*Primary Examiner* — Carlos A Azpuru
(74) *Attorney, Agent, or Firm* — Laura A. Donnelly

(57) ABSTRACT

A method of selecting skin treatment regimens, ingredients and compositions that includes measuring the levels of particular small molecule metabolites on skin both before and after product application and testing for a change in small molecule metabolite levels is disclosed.

8 Claims, 12 Drawing Sheets

Amino Acids
Peptides
Carbohydrates
Energy
Lipid
Nucleotide
Cofactors and Vitamins
Xenobiotics
N/A

Figure 2B

Ring J. (2016) Pathophysiology of Atopic Dermatitis/Eczema. In: Atopic Dermatitis. Springer, Cham PMID:16098026

METHOD OF SELECTING SKIN TREATMENT REGIMENS, INGREDIENTS AND COMPOSITIONS

FIELD OF THE INVENTION

The present invention relates to in vivo methods for measuring small molecule metabolites in skin. The methods may be employed to select skin treatments that enhance beneficial metabolite levels in skin. The present invention also relates to methods for identifying regimens, ingredients and compositions that can improve the health of skin. It also relates to the use of such regimens, ingredients and compositions to formulate skin care products.

BACKGROUND OF THE INVENTION

Skin is a complex, multi-layered and dynamic system that provides a protective covering defining the interactive boundary between an organism and the environment. It is the largest organ of the body and is vitally important to our health. Skin comprises three principal layers, the epidermis, the dermis and a layer of subcutaneous fat.

The dermis provides the epidermis with a solid support. It is also its nurturing element. It consists mainly of fibroblasts and an extracellular matrix composed mainly of collagen and elastin.

The epidermis is in contact with the external environment. Its role is to protect the body from dehydration and external aggression, whether chemical, mechanical, physical or infectious.

The epidermis is composed mainly of three types of cells, the keratinocytes, melanocytes and Langerhans cells.

The cells constituting the epidermis are delimited by a lipid domain. During differentiation, phospholipids whose role is to develop the fluid structure of cell membranes are gradually replaced by a mixture composed mainly of fatty acids, cholesterol and sphingolipids.

These lipids are organized in specific lamellar structures whose integrity depends not only on the quality of the fractions present but also on their respective proportions. This lamellar structure of lipids is responsible for the fluidity and therefore the suppleness of skin.

Lipids are also responsible for the barrier properties of the epidermis particularly the stratum corneum.

Epidermal lipids are synthesized mainly in the living epidermis. They consist mainly of phospholipids, sphingolipids, cholesterol, free fatty acids, triglycerides, cholesterol esters and alkanes. Phospholipids are essential for the constitution of cell membranes. They play an important role in the mediation of extracellular signals and the formation of free aliphatic chains used for energy production. They constitute a reservoir of free fatty acids necessary for the constitution of sphingolipids. Sphingolipids (or ceramides) are essential for maintaining the multilamellar structure of intercorneocyte lipids. They are also essential for water exchanges and the "barrier" function of the epidermis. Cholesterol plays a key role in skin hydration and in the function "barrier" of the epidermis.

Free fatty acids play a major role in the maintenance of the lamellar structure of the lipids of the stratum corneum, but also in the constitution of cell membranes where they are responsible for the membrane fluidity but also for physiological processes such as the functioning of receptors or enzymatic activity.

Lipids in the epidermis are influenced by factors such as diet, climate, season, environmental factors and/or external aggression. All these factors have the effect of altering or modifying the composition of the lipids of the skin or of reducing the amount thereof. In fact, the main consequence of these factors on lipid layers of an epidermis is drying of skin. Indeed the disorganization of the lipids when it is not a question of their disappearance, results in the increase of water loss of the skin. However, it is known that the loss of water through the lipid layers of the skin has the consequence of triggering a neosynthesis of lipids by the skin in order to reconstitute its lipid capital. Thus, regular and limited disorganization of the lipid layer by intercalating components such as penetration enhancers can constantly stimulate the lipogenesis of the skin and prepare it to respond quickly and effectively to the aggressions that it undergoes.

It is therefore important to be able to stimulate lipid synthesis of skin to maintain and/or restore their integrity.

Adding to skin's complexity is the need to keep it clean. Because of the complexity of skin and the differences in skin from season to season, it can be difficult to screen skin treatment regimens, ingredients and/or compositions to understand which ones will be better for skin health. As such, there is a need for improved methods to screen skin treatment regimens, ingredients and/or compositions.

French Published Application No. 2792728 to L'Oreal discloses a method of evaluating the effects of a product on epidermal lipogenesis that includes applying the product to the surface of a skin equivalent, measuring the variation of a marker of epidermal lipids, then making a comparison with a similar measurement for a control sample.

United States Patent Application No. 20020182112 to Unilever Home & Personal Care USA discloses an in vivo method for measuring the binding of chemical compounds or mixtures of compounds to skin constituents.

United States Patent Application No. 20180185255 to The Procter & Gamble Company discloses a method of selecting a skin cleanser that includes measuring the levels of particular ceramides on the skin both before and after product application and testing for a change in ceramide levels.

U.S. Pat. No. 8,053,003 to Laboratoires Expanscience discloses a method of treating sensitive skin, irritated skin, reactive skin, atopic skin, pruritus, ichtyosis, acne, xerosis, atopic dermatitis, cutaneous desquamation, skin subjected to actinic radiation, or skin subjected to ultraviolet radiation, comprising administering an effective amount of a composition comprising furan lipids of plant oil and thereby increasing synthesis of skin lipids.

U.S. Pat. Nos. 9,808,408 and 10,172,771 to The Procter & Gamble Company discloses a method of identifying a rinse off personal care composition that includes: (a) generating one or more control skin profiles for two or more subjects; (b) contacting at least a portion of skin of the subjects with a rinse-off test composition, rinsing the test composition off the portion of skin, extracting one or more skin samples from each of the subjects, and generating from the extracted samples one or more test profiles for the subjects; (c) comparing the one or more test profiles to the one or more control profiles and identifying the rinse-off test composition as effective for improving the stratum corneum barrier in a human subject who shows (i) a decrease in one or more inflammatory cytokines, (ii) an increase in one or more natural moisturizing factors, (iii) an increase in one or more lipids, and (iv) a decrease in total protein.

Chon et al., Keratinocyte differentiation and upregulation of ceramide synthesis induced by an oat lipid extract via the activation of PPAR pathways, Experimental Dermatology, 24:290-295 (2015), discloses that oat lipids may possess dual agonistic activities for PPARα and PPARβ/δ, increase their gene expression and induce gene differentiation and ceramide synthesis in keratinocytes, which can collectively improve skin barrier function.

Zhang et al., Topically applied ceramide accumulates in skin glyphs, Clinical, Cosmetic and Investigational Dermatology, 8:329-337 (2015), discloses a heterogeneous, sparse spatial distribution of ceramides in stratum corneum.

Ring J. (2016) Pathophysiology of Atopic Dermatitis/Eczema. In: Atopic Dermatitis. Springer, Cham PMID: 16098026, discloses the state of the art in research in atopic dermatitis, or atopic eczema.

Glatz et al., Emollient use alters skin barrier and microbes in infants at risk for developing atopic dermatitis, PLoS ONE, 13(2):e0192443 (2018), discloses that emollient use correlated with an increased richness and a trend toward higher bacterial diversity as compared to no emollient use in infants at risk for developing atopic dermatitis.

Capone et al., Effects of emollient use on the developing skin microbiome, presented at the American Academy of Dermatology Annual Meeting, 1-5 Mar. 2019, Washington D.C., USA, discloses that microbial richness is significantly greater with infant wash and lotion than with wash alone. Capone et al. also discloses that both cleansing alone and cleansing and emollient regimens were well tolerated; skin pH remained slightly acidic throughout the study in each regimen; no significant changes for dryness, redness/erythema, rash/irritation, tactile roughness or total score of objective irritation or for overall skin appearance, in either group vs. baseline at any timepoint; an increase in microbial richness seen by 2 and 4 weeks with wash and by 4 weeks with addition of lotion; by 4 weeks use, lotion use increased richness more than wash alone; mild infant wash+lotion routine may best help improve microbial richness, which may contribute to overall skin barrier health by providing the right environment for healthy skin microbes to flourish.

SUMMARY OF THE INVENTION

The present invention relates to an in vivo method for measuring small molecule metabolites in skin.

The invention also relates to a method for screening skin treatment regimens, ingredients and/or compositions, comprising: (a) measuring the level of one or more small molecule metabolites on an area of skin prior to application of the skin treatment regimen, ingredient and/or composition; (b) applying the skin treatment regimen, ingredient and/or composition to the area of skin for a period of time; (c) measuring the level of one or more small molecule metabolites after the skin treatment regimen, ingredient and/or composition application on the area of skin; wherein the skin treatment regimen, ingredient and/or composition is beneficial to the skin if the level of the one or more small molecule metabolites is at least 10% different vs. the no treatment control.

The invention also relates to a method of enhancing the amount of beneficial small molecule metabolites in skin, comprising: (a) applying a skin treatment regimen, ingredient and/or composition to skin; and (b) repeating (a) for a period of time.

These and any other methods and compositions will be described in more detail below.

BRIEF DESCRIPTION OF THE DRAWINGS

FIGS. 2A and 2B are diagrams that show the impact that treatment with (1) Johnson's CottonTouch™ Wash & Shampoo and (2) Group 2: Johnson's CottonTouch™ Wash & Shampoo and Johnson's CottonTouch™ Face & Body Lotion have on small molecule metabolites of skin.

DETAILED DESCRIPTION OF THE INVENTION

Figure 1:
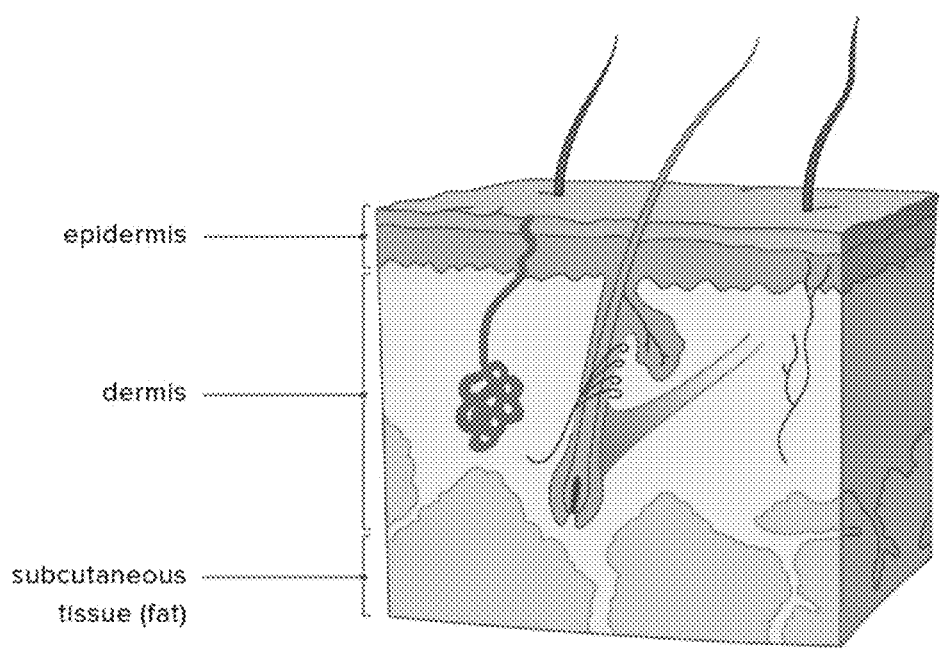
FIG. 1 is a diagram showing the three layers of skin.

The scope of the present invention will be better understood from the following description.

The devices, apparatuses, methods, components, and/or compositions of the present invention can include, consist essentially of, or consist of, the components of the present invention as well as other ingredients described herein. As used herein, "consisting essentially of" means that the devices, apparatuses, methods, components, and/or compositions may include additional ingredients, but only if the additional ingredients do not materially alter the basic and novel characteristics of the claimed devices, apparatuses, methods, components, and/or compositions.

All percentages and ratios used herein are by weight of the total composition.

Definitions

As used herein, the following terms shall have the meaning specified thereafter: "Biomarker" as used herein refers to any biological molecule (gene, protein, lipid, metabolite) that, singularly or collectively, reflect the current or predict future state of a biological system. Thus, as used herein, various biomarkers are indicators of the quality of skin. The response of skin to treatment can also be assessed by measuring one or more biomarkers.

"Ceramides" as used herein refers to a family of lipid molecules that makeup part of the stratum corneum layer of the skin. Together with cholesterol and saturated fatty acids, ceramides help the skin to be water-impermeable to help prevent water loss and also to act as a protective layer to keep unwanted microorganisms from entering the body through the skin. When the ceramide level of skin is suboptimal, the stratum corneum can become compromised. The skin can also become dry and irritated. Ceramides are composed of a fatty acid chain amide linked to a sphingoid base. There are three types of fatty acids which can be part of a ceramide. These are non-hydroxy fatty acids (N), α-hydroxy fatty acids (A), and esterified Ω-hydroxy fatty acids (EO). In addition, there are four sphingoid bases:

dihydrosphingosine (DS), sphingosine (S), phytosphingosine (P), and 6-hydroxy sphingosine (H).

"Comprising" as used herein is inclusive and does not exclude additional, unrecited elements, steps or methods. Terms as used herein that are synonymous with "comprising" include "including," "containing," and "characterized by," and mean that other steps and other ingredients can be included. The term "comprising" encompasses the terms "consisting of" and "consisting essentially of," wherein these latter terms are exclusive and are limited in that additional, unrecited elements, steps or methods ingredients may be excluded. The skin treatment regimens, ingredients and compositions of the present disclosure can comprise, consist of, or consist essentially of, the steps, methods and elements as described herein.

"Confidence level" as used herein means the probability that the value of a parameter falls within a specified range of values.

"Consumer" as used herein refers to an individual who purchases and/or uses skin treatment regimens, ingredients and/or compositions in accordance with the disclosure. In some instances, therefore, a consumer may be alternately referred to herein as a "user."

"Control surface" as used herein means a region of epithelial tissue which has not been contacted with and/or by a regimen, ingredient and/or composition which has contacted the affected surface.

"Effective amount" as used herein means an amount of a regimen, ingredient and/or composition sufficient to significantly induce a positive skin benefit, including independently or in combination with other benefits disclosed herein. This means that the content and/or concentration of active component in the regimen, ingredient and/or composition is sufficient that when the regimen, ingredient and/or composition is applied with normal frequency and in a normal amount, the regimen, ingredient and/or composition can result in the treatment of one or more undesired skin conditions. For instance, the amount can be an amount sufficient to inhibit or enhance some biochemical function occurring within the skin. This amount of active component may vary depending upon, among other factors, the type of regimen, ingredient and/or composition and the type of skin condition to be addressed.

"Epidermis" as used herein refers to the outer layer of skin, and is divided into five strata, which include the: stratum corneum, stratum lucidum, stratum granulosum, stratum spinosum, and stratum basale. The stratum corneum contains many layers of dead, anucleated keratinocytes that are essentially filled with keratin. The outermost layers of the stratum corneum are constantly shed, even in healthy skin. The stratum lucidum contains two to three layers of anucleated cells. The stratum granulosum contains two to four layers of cells that are held together by desmosomes that contain keratohyaline granules. The stratum spinosum contains eight to ten layers of modestly active dividing cells that are also held together by desmosomes. The stratum basale contains a single layer of columnar cells that actively divide by mitosis and provide the cells that are destined to migrate through the upper epidermal layers to the stratum corneum. The predominant cell type of the epidermis is the keratinocyte. These cells are formed in the basal layer and exist through the epidermal strata to the granular layer at which they transform into the cells know as corneocytes or squames that form the stratum corneum. During this transformation process, the nucleus is digested, the cytoplasm disappears, the lipids are released into the intercellular space, keratin intermediate filaments aggregate to form microfibrils, and the cell membrane is replaced by a cell envelope made of cross-linked protein with lipids covalently attached to its surface. Keratins are the major structural proteins of the stratum corneum. Corneocytes regularly slough off (a process known as desquamation) to complete an overall process that takes about a month in healthy human skin. In stratum corneum that is desquamating at its normal rate, corneocytes persist in the stratum corneum for approximately 2 weeks before being shed into the environment.

"Epithelial tissue" as used herein refers to all or any portion of the epithelia, in particular the epidermis, and includes one or more portions of epithelia that may be obtained from a subject by a harvesting technique known in the art, including those described herein. By way of example and without being limiting, epithelial tissue refers to cellular fragments and debris, proteins, isolated cells from the epithelia including harvested and cultured cells.

"Filaggrin" (filament aggregating protein) as used herein refers to a filament-associated protein that binds to keratin fibers in epithelial cells. Filaggrin is essential for the regulation of epidermal homeostasis. Within the stratum corneum, filaggrin monomers can become incorporated into the lipid envelope, which is responsible for the skin barrier function. Alternatively, these proteins can interact with keratin intermediate filaments. Filaggrin undergoes further processing in the upper stratum corneum to release free amino acids that assist in water retention.

"Metabolite" as used herein refers to the intermediate end product of metabolism. The term metabolite is usually restricted to small molecules. Metabolites have various functions, including fuel, structure, signaling, stimulatory and inhibitory effects on enzymes, catalytic activity of their own (usually as a cofactor to an enzyme), defense, and interactions with other organisms (e.g. pigments, odorants, and pheromones). A primary metabolite is directly involved in normal "growth", development, and reproduction. A secondary metabolite is not directly involved in those processes, but usually has an important ecological function.

"Metabolomics" as used herein refers to the study of the small-molecule metabolite profile of a biological organism, with the metabolome jointly representing all metabolites. The metabolome is the very end product of the genetic setup of an organism, as well as the sum of all influences it is exposed to, such as nutrition, environmental factors, and/or treatment.

"Package" includes any suitable container for personal care regimens, ingredients and/or compositions.

"Personal care composition" as used herein, refers to compositions intended for topical application to the skin. The compositions used in accordance with the present disclosure include topically applied compositions, including leave-on formulations, and rinse-off formulations in which the product is applied topically to the skin and then is subsequently rinsed within minutes from the skin with water, or otherwise wiped off using a substrate with deposition of a portion of the composition. The personal care composition used in accordance with the present disclosure is typically dispensible from a package. Thus, in some embodiments, the dispensing may be by extruding. In some embodiments the package may be a single chamber package, or a multi chamber package, or a set of discrete packages. The personal care compositions used in accordance with the present disclosure can be in the form of liquid, semi-liquid, cream, lotion or gel intended for topical application to skin.

"Rinse-off" ingredients or compositions by which is meant the ingredient or composition is applied topically to skin and then subsequently and immediately (i.e., within minutes) rinsed away with water, or otherwise wiped off using a substrate or other suitable removal means.

"Skin" is divided into three main structural layers, the outer epidermis, the inner dermis, and the subcutaneous tissue.

"Stratum corneum" as used herein, refers to the outermost layer of the epithelia, or the epidermis, and is the skin structure that provides a chemical and physical barrier between the body of an animal and the environment. The stratum corneum is a densely packed structure comprising an intracellular fibrous matrix that is hydrophilic and able to trap and retain water. The intercellular space is filled with lipids formed and secreted by keratinocytes and which provide a diffusion pathway to channel substances with low solubility in water.

"Subject" as used herein refers to a human for whom a regimen, ingredient and/or composition is tested or on whom a regimen, ingredient and/or composition is used in accordance with the methods described herein.

"Substantially free of" as used herein, unless otherwise specified, means that the personal care regimen, ingredient and/or composition comprises less than about 2%, less than about 1%, less than about 0.5%, or even less than about 0.1% of the stated ingredient. The term "free of", as used herein, means that the personal care regimen, ingredient and/or composition comprises 0% of the stated ingredient. However, these ingredients may incidentally form as a by-product or a reaction product of the other components of the personal care regimen, ingredient and/or composition.

"Surfactant" as used herein means the total of all anionic, nonionic, amphoteric, zwitterionic and cationic surfactants in a phase.

"Test ingredients and/or compositions" as used herein include and encompass purified or substantially pure ingredients and/or compositions, as well as formulations comprising one or multiple ingredients and/or compositions. Thus, non-limiting examples of test ingredients and/or compositions include water, a pharmaceutical or cosmeceutical, a product, a mixture of compounds or products, and other examples and combinations and dilutions thereof.

"Test surfaces" as used herein means a region of epithelia tissue which has been contacted with and/or by a product, such as a consumer product and/or a test regimen, ingredient and/or composition, whereby the contact of the product and/or the regimen, ingredient and/or composition on the epithelia tissue has resulted in some change, such as but not limited to, physiological, biochemical, visible, and/or tactile changes, in and/or on the epithelia tissue that may be positive or negative. In some examples, positive effects caused by regimen, ingredient and/or composition may include but are not limited to, reduction in one or more of erythema, trans-epidermal water loss (TEWL), discoloration of the skin, rash, dermatitis, inflammation, eczema, dandruff, edema and the like. The location of the affected surface will depend upon the regimen, ingredient and/or composition used or the location of some physiological, biochemical, visible, and/or tactile change in and/or on the epithelia tissue.

"Topical application", "topically", and "topical", as used herein, mean to apply the regimen, ingredient and/or composition used in accordance with the present disclosure onto the surface of the skin.

"Treating" or "treatment" or "treat" as used herein includes regulating and/or immediately improving skin appearance and/or feel.

Skin cleansers may contribute to skin dryness as the surfactants or soaps utilized within these types of products necessarily remove some of the sebum naturally occurring on the skin. Moisturizers may mitigate the drying impact of the surfactant or soap, and in some cases may positively impact the moisture of the skin such that it is better than before use.

A skin treatment regimen, ingredient and/or composition can be formulated to not only minimize any negative impact on some of the small molecule metabolites, but to enhance the small molecule metabolites in the stratum corneum for enhanced skin barrier function and hydration. This also allows for such skin treatment regimen, ingredient and/or composition to be screened for skin mildness and barrier improvement. This could be done, for example, by having subjects use the skin treatment regimen, ingredient and/or composition and measuring the impact on small molecule metabolites.

Skin Treatment Regimens

Cleansing Phase

The skin treatment regimen can include a cleansing phase.

Benefit Phase

The skin treatment regimen can include a benefit phase. The benefit phase can include the use of one or more benefit agents.

Additional optional materials can also be added to the skin cleansing composition to treat the skin, or to modify the aesthetics of the skin cleansing composition as is the case with perfumes, colorants, dyes, or the like.

Other optional materials can be those materials approved for use in cosmetics and that are described in the International Cosmetic Ingredient Dictionary and Handbook, Sixteenth Edition, Personal Care Products Council, 2016.

U.S. Pat. No. 10,267,777 to Metabolon, Inc. discloses a mass spectrometry method of measuring levels of small molecules in a sample from an individual subject to determine small molecules having aberrant levels in the sample from the individual subject, the determination being relevant to screening for a plurality of diseases or disorders in the individual subject or relevant to facilitating diagnosis of a plurality of diseases or disorders in the individual subject.

U.S. Pat. No. 8,849,577 to Metabolon, Inc. discloses a method for identifying biochemical pathways affected by an agent comprising: obtaining a small molecule profile of a sample from an assay treated with said agent, said small molecule profile comprising information regarding at least ten small molecules including identification information for the at least ten small molecules; comparing said small molecule profile to a standard small molecule profile; identifying components of said small molecule profile affected by said agent; identifying one or more biochemical pathways associated with said identified components by mapping said identified components to the one or more biochemical pathways using a collection of data describing a plurality of biochemical pathways and an analysis facility executing on a processor of a computing device, thus identifying biochemical pathways affected by said agent, wherein the plurality of biochemical pathways includes the one or more identified biochemical pathways associated with the identified components and a plurality of non-identified biochemical pathways; and storing information regarding each identified biochemical pathway and an identified component or identified components mapped to the identified biochemical pathway for each identified biochemical pathway.

U.S. Published Application No. 20160356798 to Metabolon, Inc. discloses A method of estimating de novo lipogenesis in a subject.

U.S. Published Application No. 20160019335 to Metabolon, Inc. discloses a method for analyzing metabolite data in a sample.

U.S. Published Application No. 20140287936 to Metabolon, Inc. discloses a method for identifying small molecules relevant to a disease state.

The following examples describe and demonstrate examples within the scope of the invention. The examples are given solely for the purpose of illustration and are not to be construed as limitations of the present invention, as many variations thereof are possible without departing from the spirit and scope of the invention.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

According to an embodiment, the invention is a method for evaluating the effect of a skin treatment regimen, ingredient and/or composition on the health of skin, wherein in a first step, the skin treatment regimen, ingredient and/or composition is applied to the surface of skin and left in contact with the skin for a sufficient time, and that in a second step, the variation of at least one small molecule metabolite of the epidermis is measured, and wherein the results of this measurement are evaluated with respect to a control.

In general, the time during which the skin treatment regimen, ingredient and/or composition to be tested is left in contact with the skin depends on effect that one wishes to obtain. It is at least the time necessary to see a change in the level of the specific small molecule metabolite chosen with respect to the same small molecule metabolite in an identical skin not treated. This application time can range from 1 minute to several hours or even several days. Preferably, according to the invention, the exposure time is between 5 minutes and 24 hours.

According to a variant of the invention, the skin treatment regimen, ingredient and/or composition to be tested can be applied to the skin by repeated applications at intervals of time that the experimenter can easily define at his/her convenience.

According to the invention, the variation of a small molecule metabolite of skin is measured and the results of this measurement are evaluated against a control. By small molecule metabolite of skin is meant, according to the invention, any small molecule metabolite of skin whose presence, absence or modification can be measured in response to the application to the surface of skin of the product to be tested.

The method according to the invention can thus allow the evaluation of the effects of a skin treatment regimen, ingredient and/or composition on the health of skin. This is of great interest in view of the knowledge of the consequences of the application on the skin of a skin treatment regimen, ingredient and/or composition, especially when it is a new skin treatment regimen, ingredient and/or composition.

Accordingly, it is an objective of the present invention to apply the basic science knowledge about small molecule metabolites and skin health in a rigorous and objective manner to identify and evaluate test agents for usefulness as personal care products to improve skin health. Methods are provided which enable identification and characterization of agents which positively influence cellular and tissue properties to maintain or restore health to the skin. A representative regimen is described which has been tested and positively identified as influencing statically significant changes in a variety of skin small molecule metabolites.

These and other features, aspects, and advantages of the embodiments disclosed herein will become evident to those skilled in the art from a reading of the present disclosure with the appended claims.

The present invention is based in part of discovery by the inventors that beneficial effects of skin treatment regimen, ingredient and/or composition can be detected within the tissue and cells using one or more small molecule metabolites. The inventors identified and characterized a panel of small molecule metabolites that demonstrate statistically significant changes within skin tissue in response to treatment with test skin treatment regimens, ingredients and/or compositions. In many instances, these changes have been demonstrated by the inventors to closely correlate with objective measures of skin health. As a result of the inventors' efforts, the invention provides in some embodiments a panel of small molecule metabolites, one or more of which can be used as an indicator of positive benefits of one or more test skin treatment regimens, ingredients and/or compositions on skin. In some aspects, the invention also includes specific correlations between one or more of the small molecule metabolites and one or more objective measures of skin health. Therefore, use of the small molecule biomarker panels enables the efficient screening and identification of test skin treatment regimen, ingredient and/or composition as providing one or more beneficial effects for consumer use.

Accordingly, developed in accordance with the methods described herein, the test skin treatment regimens, ingredients and/or compositions include skin treatment regimens, ingredients and/or compositions that are selected for their demonstrable ability to enhance skin health. Surface moisturizers may only be a temporary fix for dry skin. Personal care skin treatment regimens, ingredients and/or compositions formulated in accordance with the inventive methods provide benefits beyond moisturizing skin at the surface and demonstrably penetrate the skin to improve overall skin health at the cellular level, as evidenced by changes in small molecule metabolites that correlate with objective measures of skin health.

Small molecule metabolites present in the test and/or control samples can be identified using one or more techniques known in the art.

In some examples, effectiveness of treatment with a test skin treatment regimen, ingredient and/or composition is evidenced by an increase in the amount of one or more small molecule metabolites shown to correlate as increasing with increasing beneficial effects.

In some embodiments, effectiveness of treatment with a test skin treatment regimen, ingredient and/or composition is evidenced by a decrease in the amount of one or more small molecule metabolites shown to correlate as decreasing with increasing beneficial effects.

According to an embodiment, the effects of the skin treatment regimen, ingredient and/or composition on small molecule metabolites may be correlated with one or more physical measures, e.g., reduction of visual dryness, reduction of trans-epidermal water loss, and increase in skin hydration.

Also provided are methods for improving the quality of skin that are evidenced by measurable improvement in one or more small molecule metabolites. According to such embodiments, the steps further include repeating the steps of applying the skin treatment regimen, ingredient and/or composition on at least a once daily basis over a time interval of successive days, the time interval of use sufficient to permit detection of measurable improvement in at least one small molecule metabolite.

According to the various embodiments, evidence of improvement based on physical properties and small molecule metabolites is determined using general analytic methods known in the art.

The personal care skin treatment regimens, ingredients and/or compositions used in accordance with the present disclosure are used in a conventional manner for use on skin, for example, for cleansing and conditioning skin. Typically, the personal care skin treatment regimen, ingredient and/or composition used in accordance with the present disclosure are applied topically to the desired area of the skin in an amount sufficient to provide effective delivery of the actives. The skin treatment regimen, ingredient and/or composition can be applied directly to the skin or indirectly via the use of an applicator pad or brush, cleansing puff, washcloth, sponge or other implement.

The present disclosure is directed in some aspects to methods and regimens for improving or maintaining the quality of skin through use of personal care skin treatment regimens, ingredients and/or compositions. In some aspects, the methods are useful for sustaining consumer use of a treatment for skin.

In some embodiments, the skin treatment regimen, ingredient and/or composition can comprise additional benefit agents, such as fragrances, and other optional agents. It is contemplated according to the various embodiments that the two or more skin benefit agents are delivered in varying relative quantities. It will be appreciated that additional benefit agents may be delivered together with one or the other benefit agents such that quantities of such additional benefit agents varies synchronously with one of the other benefit agents. It will further be appreciated that each of two, three or more benefit agents may each be delivered in varying relative quantities that are not in synchrony with any of the other benefit agents.

The following examples further describe and demonstrate embodiments within the scope of the present disclosure. The examples are given solely for the purpose of illustration and are not to be construed as limitations of the present disclosure, as many variations thereof are possible without departing from the spirit and scope hereof.

Except where specific examples of actual measured values are presented, numerical values referred to herein should be considered to be qualified by the word "about."

All documents cited in the Detailed Description are, in relevant part, incorporated herein by reference; the citation of any document is not to be construed as an admission that it is prior art with respect to the present disclosure. To the extent that any meaning or definition of a term in this document conflicts with any meaning or definition of the same term in a document incorporated by reference, the meaning or definition assigned to that term in this document shall govern.

While particular embodiments as disclosed herein have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

EXAMPLE

Treatment Groups

Infants at the indicated ages were treated in accordance with below.

Group 1: Johnson's CottonTouch™ Wash & Shampoo[1]

[1] Contains the following ingredients: water, cocamidopropyl betaine, PEG-80 sorbitan laurate, decyl glucoside, cotton, acrylates/C10-30 alkyl acrylate crosspolymer, phenoxyethanol, sodium benzoate, fragrance [Hedione, Globalide®, Florosa, Isobornyl Cyclohexanol, Tetrahydro Linalool, Ethylene Brassylate, Dipropylene Glycol, Sandranol®, Magnolan, Agrumex], coco-glucoside, glyceryl oleate, sodium hydroxide, ethylhexylglycerin, tetrasodium glutamate diacetate.

Group 2: Johnson's CottonTouch™ Wash & Shampoo and Johnson's CottonTouch™ Face & Body Lotion[2]

[2] Contains the following ingredients: water, glycerin, isopropyl palmitate, cotton, dimethicone, phenoxyethanol, cetearyl olivate, fragrance [Hedione, Globalide®, Florosa, Isobornyl Cyclohexanol, Tetrahydro Linalool, Ethylene Brassylate, Sandranol®, Dipropylene Glycol, Magnolan, Agrumex, Heliotropin], sorbitan olivat*, carbomer, acrylates/C10-30 alkyl acrylate crosspolymer, caprylyl glycol, 1,2-hexanediol, sodium hydroxide, ethylhexylglycerin, tropolone.

Timepoints

Study Baseline (babies, age 3-6 months)

2 Week treatment (babies, ages 3-6 months)

4 Week treatment (babies, ages 3-6 months)

Regression—no treatment (babies, ages 3-6 months)

Assessments

The infants were assessed as follows.

Principal Investigator assessment of objective irritation—dryness, redness/erythema, rash/irritation, tactile roughness and overall skin appearance Caregiver assessment of baby's skin for irritation, dryness, softness, roughness and overall skin appearance Caregiver questionnaire on breastfeeding, delivery, touch and environment Non-invasive measures of skin pH, moisture, D-Squame tapes & skin microbiome on forearm, forehead, and buttock Safety: adverse events captured throughout the study Samples for Metabolomic Analysis were Prepared as Follows Minimal invasive methods are desirable to enable more dynamic and repetitive skin sampling over time in relation to treatment, environment and disease flares. Tape stripping, which reduces discomfort, potential infection and scarring and which minimizes inferring substances from deeper layers of the epidermis, was used to measure components in the stratum corneum.

TABLE 1

| Matrix | Group 1 V1 Baseline | Group 1 V4 Day 28 | Group 2 V2 Baseline | Group 2 V4 Day 28 | Blank Strips | Total Number of Samples |
|---|---|---|---|---|---|---|
| D-Squame | 9 | 10 | 11 | 11 | 2 | 43 |

The number of samples for each treatment are shown in Table 1.

Figure 2A:
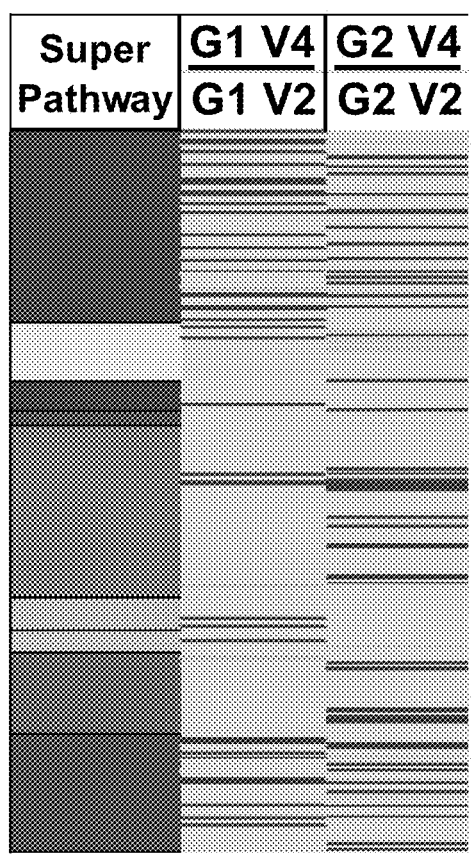
Figures 3A, 3B:
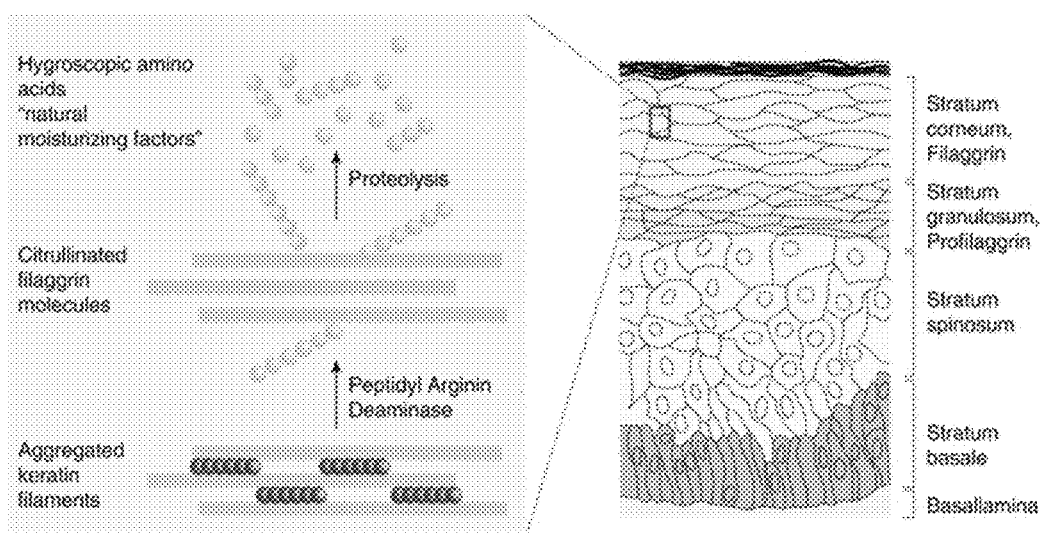
FIGS. 3A and 3B are diagrams from Ring 2016 showing the pathophysiology of atopic dermatitis/eczema.
Figure 4:
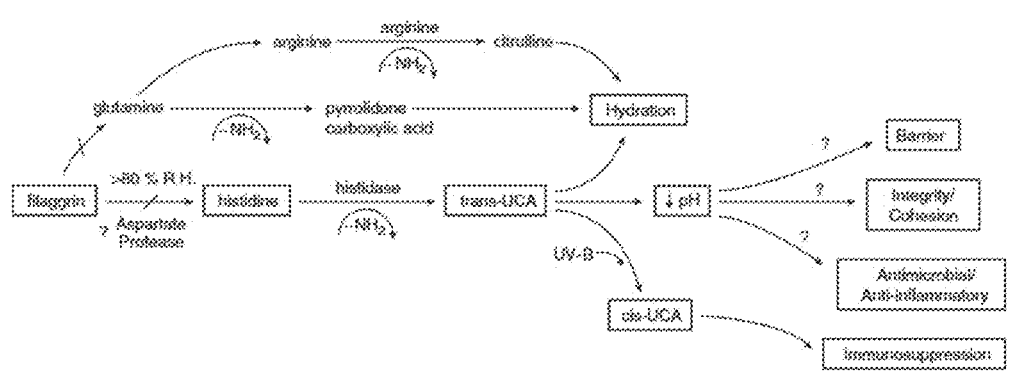
FIG. 4 is a diagram showing a pathway for filaggrin metabolism.
Figures 5A, 5B, 5C:
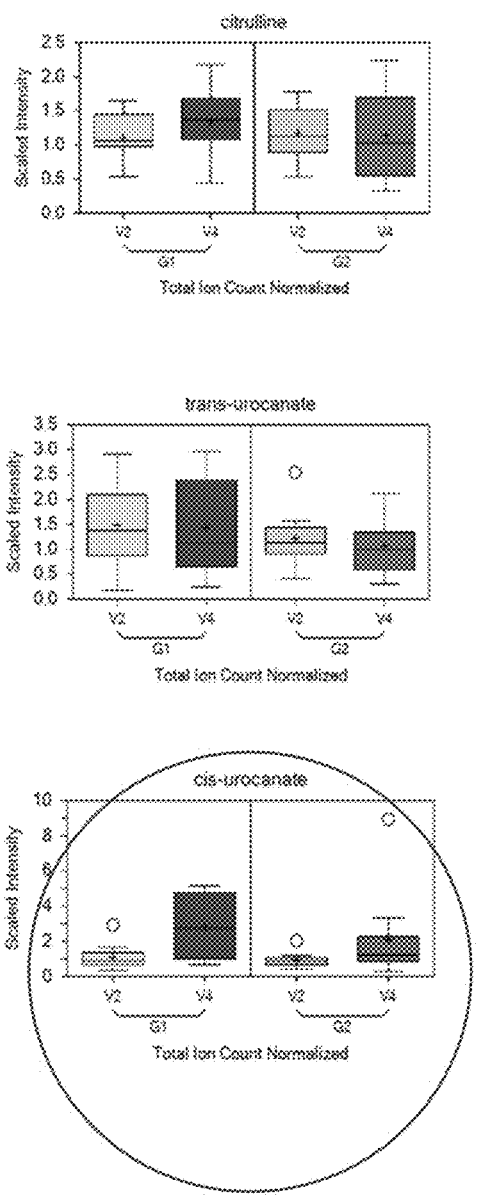
FIGS. 5A, 5B and 5C show the differences observed for citrulline, trans-urocanate and cis-urocanate, respectively.

Groups 1 and 2 refer to the different treatments above.
V2: Baseline visit
V4: End of treatment visit The data show that the two treatments have distinct effects on levels of small molecule metabolites. See FIGS. 2A and 2B.

The number of changes observed for small molecule metabolites for each treatment are shown in Table 2.

TABLE 2

| Summary Counts Two Way ANOVA | $\frac{G1V4}{G2V2}$ | $\frac{G2V4}{G2V2}$ |
|---|---|---|
| Total number of biochemicals with p≤0.05 | 39 | 50 |
| Biochemicals (↑↓) | 37 \| 2 | 33 \| 17 |
| Percent Change | 10% | 13% |

The potential impact of skin routine on filaggrin turnover
The data show that treatment 1 and treatment 2 may have opposing impacts on protein degradation. See Table 3.

TABLE 3

| Biochemical Name | $\frac{G1V4}{G1V2}$ | $\frac{G2V4}{G2V2}$ |
|---|---|---|
| Glycine | 1.15 | 1.02 |
| Serine | 1.09 | 0.98 |
| threonine | 1.15 | 0.03 |
| Alanine | 0.99 | 1 |
| Aspartate | 1.34 | 1.03 |
| Asparagine | 1.12 | 0.94 |
| Glutamate | 0.96 | 0.82 |
| Glutamine | 1.17 | 1 |
| Histidine | 1.05 | 0.87 |
| Lysine | 1.21 | 0.91 |
| Phenylalanine | 1.23 | 0.9 |
| Tyrosine | 1.21 | 0.86 |
| Tryptophan | 1.23 | 0.94 |
| Leucine | 1.2 | 0.93 |
| Isoleucine | 1.14 | 0.96 |
| Valine | 1.15 | 1 |
| Methionine | 0.9 | 1 |
| Cysteine | 1.08 | 0.64 |
| Arginine | 1.03 | 0.8 |
| Proline | 1.11 | 1.04 |

Results:
Following treatment: small increases of amino acids for G1 and small decreases for G2.

Washing (G1 and G2) may mildly dry the skin which would result in slightly higher rates of protein breakdown and NMF generation.

In G2 the lotion induces a moist environment that counters the slightly increased rates of protein breakdown. This effect may be attributed to the glycerol (3% in the lotion).

Increased cis-UCA (cis-urocanate) observed points to UV (ultraviolet) exposure for both groups.

Table 4 shows the differences observed for citrulline, trans-urocanate and cis-urocanate, respectively.

TABLE 4

| Biochemical Name | $\frac{G1V4}{G1V2}$ | $\frac{G2V4}{G2V2}$ |
|---|---|---|
| Citrulline | 1.22 | 0.97 |
| Trans-urocanate | 0.97 | 0.87 |
| Cis-urocanate | 2.5 | 2.21 |

Figure 6:
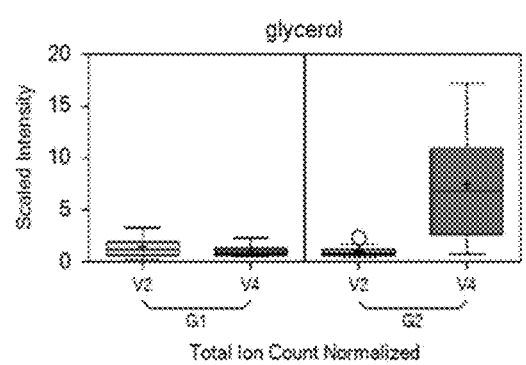
FIG. 6 shows the differences observed for glycerol.
Figure 7:
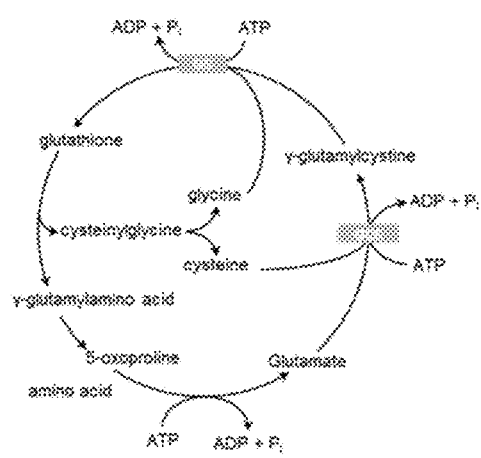
FIG. 7 is a diagram showing a pathway for γ-glutamyl amino acids metabolism.
Figure 8A:
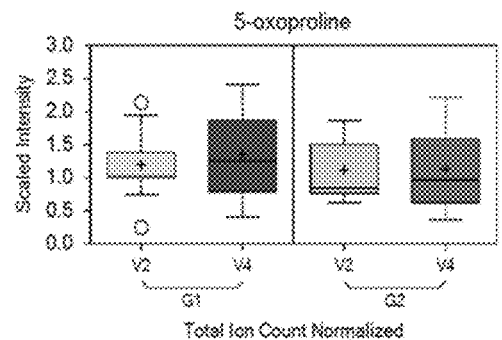
FIGS. 8A, 8B and 8C show the differences observed for 5-oxoproline, gamma-glutamyl-epsilon-lysine and gamma-glutamylglutamin, respectively.
Figure 8B:
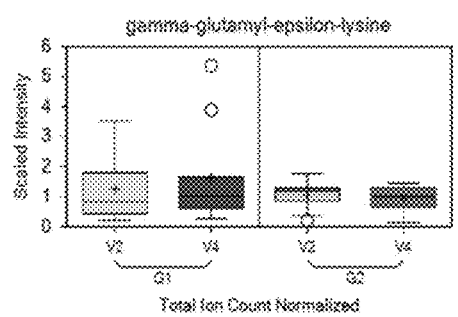
Figure 8C:
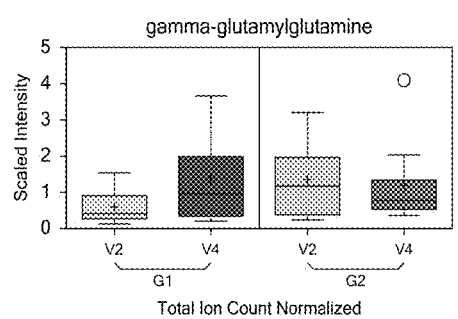
Figure 9:
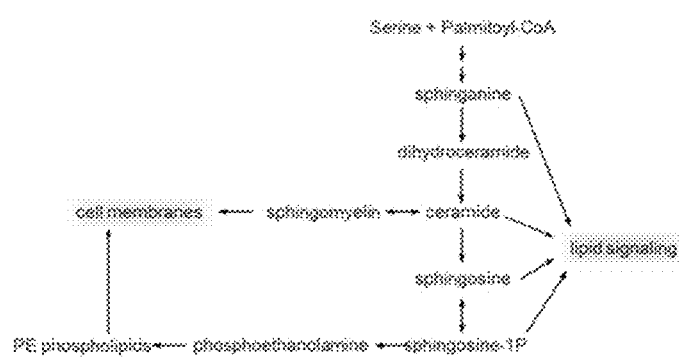
FIG. 9 is a diagram showing a pathway for ceramide metabolism.
Figure 10A:
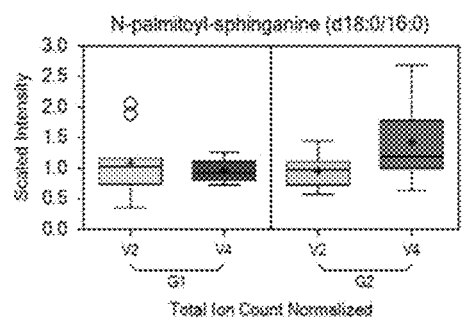
FIGS. 10A, 10B and 10C show the differences observed for N-palmitoyl-sphinganine, N-palmitoyl-sphingosine and ceramide, respectively.
Figure 10B:
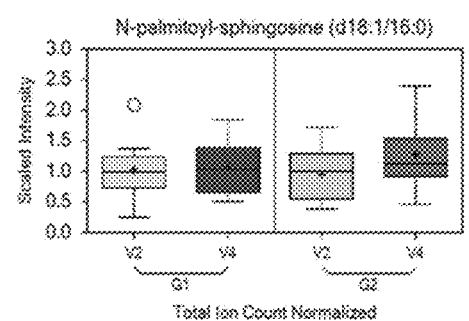
Figure 10C:
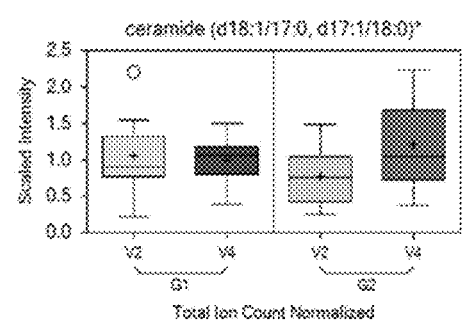
Figure 11:
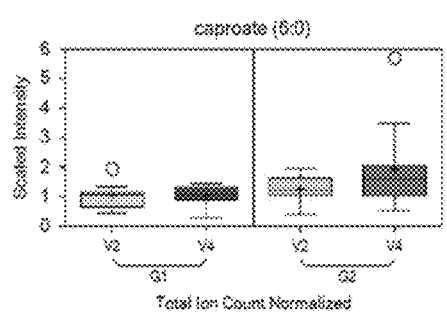
FIG. 11 shows the differences observed for caproate.

The data show that glycerol increased 7-8 times following G2 treatment. See FIG. 6 and Table 5.

TABLE 5

| Biochemical Name | $\frac{G1V4}{G1V2}$ | $\frac{G2V4}{G2V2}$ | $\frac{G2V2}{G1V2}$ | $\frac{G2V4}{G1V4}$ |
|---|---|---|---|---|
| Glycerol | 0.73 | 7.37 | 0.7 | 7.13 |
| Glycerol-3-phosphate | 1.12 | 8.24 | 0.45 | 3.35 |

Observations

Glycerol is a polyol organic osmolyte and humectant supporting SC hydration.

The sebaceous gland is a primary contributor to the endogenous glycerol pool (PMID: 12713573).

Exogenous glycerol (in the lotion formula) is most likely the reason for the increase in glycerol and glycerol-3-phosphate following treatment in G2.

Glycerol phosphate increase suggests glycerol is being captured inside the cells.

The data show that γ-glutamyl amino acids increased following G1 treatment and slightly decreased with G2 treatment.

TABLE 6

| Biochemical Name | $\frac{G1V4}{G1V2}$ | $\frac{G2V4}{G2V2}$ | $\frac{G2V2}{G1V2}$ | $\frac{G2V4}{G1V4}$ |
|---|---|---|---|---|
| 5-oxoproline | 1.13 | 1.01 | 0.93 | 0.84 |
| Gamma-glutamyl alanine | 1.2 | 0.92 | 1.36 | 1.04 |
| Gamma-glutamylglutamate | 1.38 | 0.7 | 1.92 | 0.97 |
| Gamma-glutamylglutamine | 2.28 | 0.88 | 2.26 | 0.88 |
| Gamma-glutamylglycine | 1.21 | 0.93 | 1.29 | 0.99 |
| Gamma-glutamylhistidine | 1.07 | 0.75 | 1.34 | 0.94 |
| Gamma-glutamylisoleucine* | 1.25 | 0.84 | 1.33 | 0.89 |
| Gamma-glutamylleucine | 1.38 | 0.86 | 1.63 | 1.02 |
| Gamma-glutamyl-alpha-lysine | 1.3 | 0.82 | 1.29 | 0.81 |
| Gamma-glutamyl-epsilon-lysine | 1.31 | 0.9 | 0.84 | 0.58 |
| Gamma-glutamylmethionine | 1.4 | 0.8 | 1.71 | 0.98 |
| Gamma-glutamylphenylalanine | 1.32 | 0.81 | 1.51 | 0.93 |
| Gamma-glutamylthreoni ne | 1.09 | 0.85 | 1.22 | 0.95 |
| Gamma-glutamyltryptohpan | 1.24 | 0.99 | 1.53 | 1.22 |
| Gamma-glutamyltyrosine | 1.25 | 0.87 | 1.29 | 0.9 |
| Gamma-glutamylvaline | 1.25 | 0.87 | 1.36 | 0.95 |
| Gamma-glutamylserine | 1.26 | 0.89 | 1.41 | 1 |
| Gamma-glutamylcitrulline* | 1.93 | 1.12 | 1.57 | 0.91 |

The increase in the levels of gamma-glutamyl amino acids in G1 point toward an upregulated GGT system which may reflect the need to repair the stratum corneum to reduce water loss.

Ceramide levels increased following the G2 treatment.

TABLE 7

| Sub Pathway | Biochemical Name | $\frac{G1V4}{G1V2}$ | $\frac{G2V4}{G2V2}$ | $\frac{G2V2}{G1V2}$ | $\frac{G2V4}{G1V4}$ |
|---|---|---|---|---|---|
| Sphingolipid Synthesis | Sphinganine | 0.83 | 0.93 | 0.57 | 0.64 |
| | Sphingadienine | 0.82 | 0.77 | 0.64 | 0.6 |
| | phytosphingosine | 0.73 | 0.76 | 0.5 | 0.51 |
| Dihydro-ceramides | N-palmitoyl-sphiganine (d18:0/16:0) | 0.88 | 1.51 | 0.87 | 1.49 |
| Ceramides | N-palmitoyl-sphigosine (d18:1/16:0) | 1.05 | 1.34 | 0.92 | 1.18 |
| | N-(2-hydroxypalmitoyl)-sphingosine (d18:1/16:0(2OH)) | 0.93 | 1.3 | 0.87 | 1.21 |
| | Ceramide (d18:1/14:0, d16:1/16:0)* | 0.92 | 1.14 | 0.98 | 1.22 |
| | Ceramide (d18:1/17:0, d17:1/18:0)* | 0.95 | 1.56 | 0.74 | 1.21 |
| | Ceramide (d18:1/20:0, d16:1/22:0, d20:1/18:0)* | 0.87 | 1.31 | 0.8 | 1.2 |
| Sphingosines | Sphingosine | 0.77 | 0.87 | 0.55 | 0.62 |
| | Hectadeca-sphingosine (d17:1) | 0.92 | 0.85 | 0.6 | 0.55 |
| | Eicosanoyl-sphingosine (d20:1)* | 0.8 | 0.81 | 0.6 | 0.62 |

Observations

Ceramides increased following the G2 routine.

Ceramides play an important role in maintaining the structure and barrier function of the skin. Increases in ceramide levels could be a sign of increased ceramide synthesis.

Subtly increased fatty acids following G2 treatment. See Table 8.

TABLE 8

| Sub Pathway | Biochemical Name | $\frac{G1V4}{G1V2}$ | $\frac{G2V4}{G1V1}$ | $\frac{G2V2}{G1V2}$ | $\frac{G2V4}{G1V4}$ |
|---|---|---|---|---|---|
| Medium Chain Fatty Acid | Caproate (6:0) | 1.01 | 1.55 | 1.22 | 1.87 |
| | Heptanoate (7:0) | 0.89 | 0.97 | 1.2 | 1.31 |
| | Caprylate (8:0) | 1.13 | 1.35 | 1.16 | 1.39 |
| | Caprate (10:0) | 1.24 | 1.18 | 1.03 | 0.98 |
| | Cis-4-decanoate (10:1n6)* | 1.34 | 0.83 | 1.2 | 0.75 |
| | (2 or 3)-decanoate (10:1n7 or n8) | 0.94 | 1.07 | 0.95 | 1.08 |
| | Undecanoate (11:0) | 0.82 | 0.98 | 1.03 | 1.24 |
| | 5-dodecanoate (12:1n7) | 0.97 | 1.14 | 0.86 | 1.01 |
| Long Chain Saturated Fatty Acid | Myristate (14:0) | 1.34 | 1.3 | 0.94 | 0.91 |
| | Pentadecanoate (15:0) | 0.78 | 1.24 | 1.02 | 1.61 |
| | Palmitate (16:0) | 0.87 | 1.03 | 0.91 | 1.07 |
| | Margarate (17:0) | 0.8 | 1.18 | 0.85 | 1.25 |
| | Stearate (18:0) | 0.82 | 1.07 | 0.82 | 1.05 |
| | Arachidate (20:0) | 0.83 | 1.1 | 0.83 | 1.1 |
| Long Chain monounsaturated Fatty Acid | Myristoleate (14:1n5) | 0.77 | 1.74 | 0.92 | 2.07 |
| | Palmitoleate (16:1n7) | 0.63 | 1.92 | 0.83 | 2.52 |

TABLE 8-continued

| Sub Pathway | Biochemical Name | $\frac{G1V4}{G1V2}$ | $\frac{G2V4}{G1V1}$ | $\frac{G2V2}{G1V2}$ | $\frac{G2V4}{G1V4}$ |
|---|---|---|---|---|---|
| Long Chain Polyunsaturated Fatty Acid (n3 and n6) | Tetradecadienoate (14:2)* | 1.37 | 1.07 | 0.95 | 0.74 |
| | Hexadecadienoate (16:2n6) | 0.73 | 2.23 | 0.68 | 2.09 |
| | Linoleate (18:2n6) | 4.25 | 1.4 | 0.63 | 0.21 |

Fold-change heat map that allows the extrapolation of potential class differences.

Fold changes greater than 1, fold changes less than 1, and no fold changes were observed. Caproate (6:0) (G2 V4/G1 V4) is a biochemical that exhibited statistical significance with $p<0.05$, while Caproate (6:0) (G2 V4/G2 V2) and Fleptanoate (G2 V4/G1 V4) are biochemicals that show trending differences with $0.05<p<0.10$.

Results

There was a tendency of fatty acids to increase in the G2 group, likely due to the presence of oleate (0.75%) and isopropyl palmitate (2%) in the formula.

Most long chain fatty acids decreased in the G1 group.

Fatty acids are more susceptible to disruption from cleansing products.

Free fatty acids are necessary for the formation of the lipid bilayer in the stratum corneum (barrier integrity).

These data suggest that the fatty acid profile is either maintained or increased following G2 treatment.

Medium chain fatty acids (a major component of coconut oil) may demonstrate anti-microbial effects (PMID: 23971051, 21333271).

Unsaturated fatty acids are necessary for proper sebaceous gland and hair follicle formation (PMID: 16118274, 16118274).

Summary of Results

The two treatments have distinct effects on levels of metabolites.

Wash alone (G1):
   Slightly increased levels of amino acids—likely due to SC drying following wash
   Increased levels of gamma-glutamyl amino acids—likely in response to repair SC barrier Wash+lotion (G2):
   Slightly decreased levels of amino acids—reflects prevention of effects of drying
   Increased levels of glycerol and its metabolism—due to the presence of glycerol in the lotion
   Increased levels of ceramides
   Patterns of increased levels of fatty acids enhanced barrier function Both treatments:
   Increased levels of cis-UCA—indicates UV exposure
   No effect on cholesterol levels While few metabolites linked to microbial metabolism were detected, shifts in a variety of metabolites may be related to microbial metabolism (medium chain fatty acids, salicylate).

It will be understood that, while various aspects of the present disclosure have been illustrated and described by way of example, the invention claimed herein is not limited thereto, but may be otherwise variously embodied according to the scope of the claims presented in this and/or any derivative patent application.

The invention claimed is:

1. A minimally invasive method of screening a skin treatment regimen, ingredient and/or composition for benefit to skin of infants, comprising: a) measuring the level of one or more small molecule metabolites in an area of skin of an infant prior to application of the skin treatment regimen, ingredient and/or composition, wherein the one or more small molecule metabolites is a gamma-glutamyl amino acid selected from the group consisting of gamma-glutamyl-epsilon-lysine and gamma-glutamylglutamine; b) applying the skin treatment regimen, ingredient and/or composition to the area of skin of said infant for a period of time; c) measuring the level of the said one or more small molecule metabolites after the skin treatment regimen, ingredient and/or composition application; wherein the skin treatment regimen, ingredient and/or composition is of benefit to skin if within a confidence level of greater than 90% the level of the one or more small molecule metabolites changes vs. the no treatment control.

2. The method of claim 1, wherein the test skin treatment regimen, ingredient and/or composition is left in contact with skin for an application time between about 1 minute to about 4 weeks.

3. The method of claim 2, wherein the application time is at least about 7 days.

4. The method of claim 2, wherein the application time is at least about 21 days.

5. The method of claim 2, wherein the application time is between about 5 minutes and about 24 hours.

6. The method of claim 1, wherein the skin treatment regimen, ingredient and/or composition enhances one or more attributes selected from the group consisting of reduction of visual dryness, reduction of trans-epidermal water loss, and increase in skin hydration.

7. The method of claim 1, wherein the skin treatment regimen, ingredient and/or composition is of benefit to skin if within a confidence level of greater than 95% the level of the one or more small molecule metabolites changes vs. the no treatment control.

8. The method of claim 1, wherein tape stripping is employed to obtain said one or more small molecule metabolites.

* * * * *